US009351961B2

(12) United States Patent
Sedel

(10) Patent No.: US 9,351,961 B2
(45) Date of Patent: *May 31, 2016

(54) METHOD OF TREATING MULTIPLE SCLEROSIS

(71) Applicant: Assistance Publique Hopitaux De Paris, Paris (FR)

(72) Inventor: Frédéric Sedel, Paris (FR)

(73) Assignee: Assistance Publique Hopitaux De Paris, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/458,625

(22) Filed: Aug. 13, 2014

(65) Prior Publication Data

US 2014/0348920 A1 Nov. 27, 2014

Related U.S. Application Data

(63) Continuation of application No. 13/644,615, filed on Oct. 4, 2012, now Pat. No. 8,835,487.

(30) Foreign Application Priority Data

Jul. 26, 2012 (FR) ...................................... 12 57254

(51) Int. Cl.
  *A61K 31/4188* (2006.01)
  *A61K 31/395* (2006.01)
(52) U.S. Cl.
  CPC ........... *A61K 31/4188* (2013.01); *A61K 31/395* (2013.01)
(58) Field of Classification Search
  None
  See application file for complete search history.

(56) References Cited

U.S. PATENT DOCUMENTS

| 5,789,401 | A  | 8/1998  | McCarty |
| 2007/0231405 | A1 | 10/2007 | Gorban  |
| 2013/0084334 | A1 | 4/2013  | Sedel   |

FOREIGN PATENT DOCUMENTS

| BG | 66011 | 10/2010 |
| WO | 2004/017766 A1 | 3/2004 |
| WO | 2011124571 A1 | 10/2011 |

OTHER PUBLICATIONS

Anagnostouli, et al., "Biotin in CSF and Serum in Patients with Multiple Sclerosis," J. Neurological Sciences, vol. 150. Suppl. 1, p. S47, Abstract 1-31-03 (Sep. 1997).
Darin, et al., 3-Methylcrotonyl, CoA Carboxylase Deficiency and Severe Multiple Sclerosis, 36 Pedatric Neurology, 132-34 (2007).
Bruck "The pathology of multiple sclerosis is the result of focal inflammatory demyelination with axonal damage," Abstract, J. Neurol., 252, Suppl. 5:3-9 (Nov. 2005).
Politte et al., Neuropsychiatric Manifestations of Multiple Sclerosis, 10 Prim Care Companion, J. Clin. Psychiatry, 318, 319-20 (2008).
Baumgartner, M., "3-Methylcrotonyl-CoA Carboxylase Deficiency," Orphanet Encyclopedia, (2005), pp. 1-7.
Breedon, C., "Aunt Cathy's Guide to Nutrition: Nutrition Issues in Multiple Sclerosis," MeritCare Health System (2009, pp. 1-29.
Darin et al., "3-Methylcrotonyl-CoA Carboxylase Deficiency and Severe Multiple Sclerosis," Pediatric Neurology, vol. 36, No. 2, (2007), pp. 132-134.
Shirazi et al., "Dietary Supplementation in Iranian Multiple Sclerosis Patients," J. Med. Sci., vol. 7, No. 3 (2007), pp. 413-417.
Yang et al., "Spinal Cord Demyelination Associated with Biotinidase Deficiency in 3 Chinese Patients," Journal of Child Neurology, vol. 22, No. 2 (2007), pp. 156-160.
English language abstract from esp@cenet of BG 66011 (B2) published Oct. 29, 2010.
Chakraborty, G, et al., "Fatty acid synthesizing enzymes intrinsic to myelin," Molecular Brain Research, vol. 112, pp. 46-52 ( 2003).
Chaudhuri, A., et al., "Multiple Sclerosis is Not an Autoimmune Disease," Arch Neurol, vol. 61, pp. 610-612 (2004).
Tong, L., "Structure and function of biotin-dependent carboxylases," Cell. Mol. Life Sci., vol. 7, pp. 863-891, (2013) (published online Aug. 7, 2012).
Stys, P.K. et al., "Will the real multiple sclerosis please stand up?", Nature Reviews/Neuroscience, vol. 13, pp. 507-514 and Erratum (1 page) (Jul. 2012).
Luessi, F. et al., "Neurodegeneration in multiple sclerosis: novel treatment strategies," Expert Rev. Neurother., vol. 12, No. 9, pp. 1061-1077 (2012).
Klenner, F., "Response of Peripheral and Central Nerve Pathology to Mega-Doses of the Vitamin B-Complex and Other Metabolites—Part 1," Journal of Applied Nutrition, vol. 25 (18 pages), (1973).
Klenner, F., "Response of Peripheral and Central Nerve Pathology to Mega-Doses of the Vitamin B-Complex and Other Metabolites—Part 2," Journal of Applied Nutrition, vol. 25 (11 pages), (1973).
"Vitamins Fight Multiple Sclerosis," Orthomolecular Medicine News Service, 2 pages. (Oct. 4, 2006).
Rabin, B. et al., "Inhibition of Experimentally Induced Autoimmunity in Rats by Biotin Deficiency," American Institute of Nutrition, vol. 113(11):2316-2322, (Nov. 1983).
M. Anagnostouli et al., "Jan. 31, 2003 Biotin in CSF and serum in patients with multiple sclerosis," Journal of the Neurological Sciences, vol. 150, supplement 1, p. S47, Sep. 1997.
Zhuolin Liu et al., "Multiple sclerosis is an autoimmune disease," Neurogenetic Diseases, People's Medical Publishing House, p. 478, Apr. 2002.

*Primary Examiner* — H. Sarah Park
(74) *Attorney, Agent, or Firm* — Rothwell, Figg, Ernst & Manbeck, P.C.

(57) ABSTRACT

The invention provides methods for treating multiple sclerosis by administering biotin. The invention also provides methods for treating sequelae after multiple sclerosis attacks by administering biotin.

18 Claims, 1 Drawing Sheet

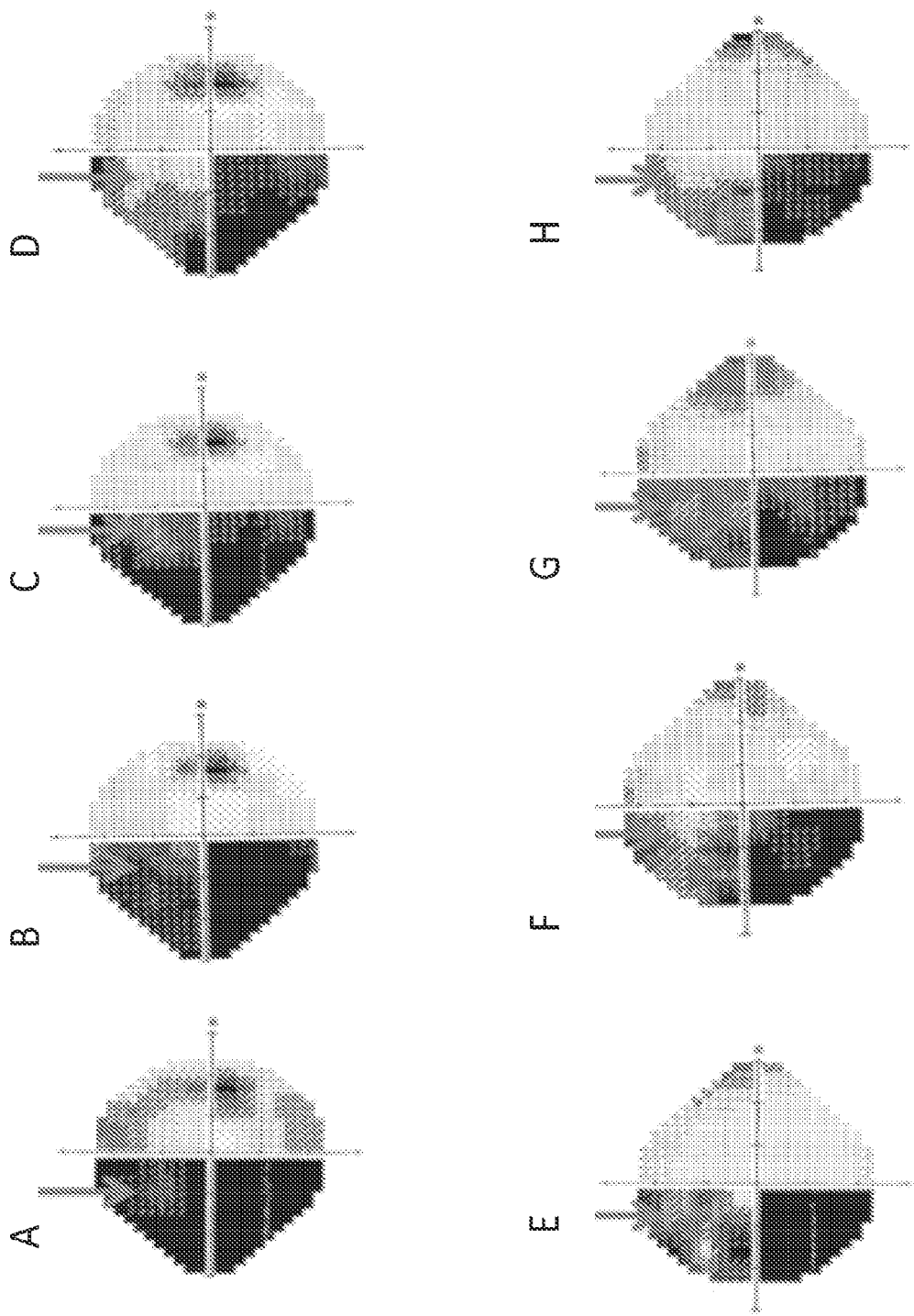

METHOD OF TREATING MULTIPLE SCLEROSIS

This application is a continuation of U.S. Ser. No. 13/644,615, filed Oct. 4, 2012, now U.S. Pat. No. 8,835,487, which claims priority to French Application 12/57254, filed Jul. 26, 2012. These prior applications are incorporated herein by reference in their entireties.

The invention relates to the treatment of multiple sclerosis, and in particular of the progressive forms and of the neurological sequelae after attacks of the disease.

Multiple sclerosis (MS) is a frequent and disabling neurological disease characterized by multifocal destruction of central nervons system myelin.

The prevalence of MS in Europe is approximately 1/2000 inhabitants (Noseworthy et al., 2000). The disease typically begins between the ages of 20 and 30 and affects twice as many women as men. In 80% of cases, the disease initially evolves through attacks which result completely or with sequelae in a few weeks or months (pure remitting phase or emitting phase with sequelae). However, in 40% to 70% of cases, patients who experience an initially remitting evolvement subsequently evolve towards a progressive form (secondary progressive form). In 20% of patients, the evolvement is immediately progressive without attacks (primary progressive form).

For patients who experience an evolvement via regressive attacks, the remissions are less complete over time, resulting in functional sequelae, the ability to walk being lost on average 20 years after the beginning of the disease.

Thus, the conventional form of multiple sclerosis can have three evolutive modes:

Relaxing-remitting form: exacerbations alternating with remissions during which partial or total recovery is observed. The remissions can last months or years. The exacerbations can occur spontaneously or be triggered post-partum or certain vaccinations.

Primary progressive form: The disease evolves progressively without remissions, with the possibility of evolutive plateau during which the disease does not progress. Contrary to the cyclic tendency, there are no clear exacerbations.

Secondary progressive form: This form follows on from a remitting form which begins with attacks alternating with remissions, followed by a gradual progression of the disease without identifiable attacks.

Pyramidal syndrome marks the beginning of (reveals) the disease in 20% of cases, and manifests itself through walking problems with high fatigability, spasticity, exaggerated reflexes in the lower limbs, the presence of a Babinski sign, no abdominal cutaneous reflexes. At the end of the attack, the Babinski sign often remains as a sequela.

Retrobulbar optic neuritis is also an indication of the disease in close to a third of cases: it is the most evocative symptom. It manifests itself for the patient through a rapid and profound decrease in visual acuity, ocular and orbital pain, increased with eye movements, central or cecocentral scotoma and colour blindness (dyschromatopsa of the red-green axis). At the acute stage, the back of the eye is normal, and it is only after about 15 days that atrophy of the papilla occurs, testifying to the damage to the optic nerve and sometimes persistent as a sequela. The visual evoked potentials are impaired, with slowing of the P100 wave.

Sensory problems are common. They are essentially subjective: paresthesia, pins and needles, Lhermitte's sign (electric shock sensation running down the spine when flexing the neck). A posterior cordonal syndrome with deep sensory disorders is sometimes found, and more rarely involvement of the spinothalamic trackt with thermalgesic anaesthesia. Facial pain (or, conversely, anaesthesia) is possible in the event of the trigeminal nerve being affected in its bulbar portion.

The disease may also manifest itself through:

A vestibular syndrome combining rotary vertigo, nystaqmus and ataxia;

A cerebellar syndrome. Demyelinated plaques are frequent in the cerebellum and in the posterior fossa, which can produce a cerebellar syndrome with an unstable upright stance, walking as if inebriated, movements which are dysmetric, etc.;

Diplopia consisting of a sensation of double vision due to paralysis of one or more oculomotor muscles. Internuclear ophthalmoplegia is possible in the event of involvement of the posterior longitudinal bundles (which link the nuclei of the oculomotor nerves and ensure that they operate harmoniously), which manifests itself in the lateral gaze through an incomplete adduction of one eye associated with nystagmus of the eye in abduction;

Genito-sphincteric disorders are frequent and are linked to spinal cord involvement. They manifest themselves through urinary urgency (or urinary retention), constipation and impotence. These disorders are a source of acute urine retention, and urinary infections;

Facial paralysis;

Asthenia (fatigue), a frequent symptom of multiple sclerosis, is sometimes the one which is the most debilitating.

Multiple sclerosis is generally considered to be an autoimmune disease which. occurs on a particular genetic background (Weiner, 2004; Chaudhuri et al., 2004). From the neuropathological point of view, the disease is characterized by demyelinated plaques, well-defined hypocellular regions, within which are observed scarcity of myelin, an astrocytic gliosis and sometimes an inflammatory infiltrate which, when it is present, attests to the active nature of the disease. With time (but sometimes early on), there are also irreversible axonal lesions, the mechanism of which is poorly understood.

Thus, it is possible to distinguish two components in the physiopathology of multiple sclerosis: (1) an inflammatory component, responsible for the evolutive attacks, and beginning with the arrival of CD4+ T lymphocytes in the central nervous system (Weiner, 2004), and (2) a degenerative component, the mechanism of which is for the moment poorly understood (Chaudhuri et. al., 2004).

Interferon beta and glatiramer acetate have proven to be effective in multiple sclerosis (attacks less numerous and less severe, improvement of lesions visible by MRI, sometimes a less evolutive nature of the handicap).

The indications for interferon treatment are remitting MS with at least two attacks over the previous two or three years, or secondary progressive MS with persistence of attacks (continuous and progressive worsening, without remission between the acute phases). The current tendency is to begin the treatment early, as soon as the first attack occurs under certain conditions since it could then reduce the functional sequelae. However, the long-term efficacy remains disputed (Filippini P. Munari L, Incorvaia B et al. Interferons in relapsing remitting multiple sclerosis: a systematic review [archive], Lancet, 2003; 361: 545-552).

Glatiramer acetate, for its part, is a copolymer consisting of several amino acids. it appears to space out the attacks in ambulatory patients (who can still walk on their own) suffering from multiple sclerosis evolving through attacks, of relapsing/remitting type, characterized by at least two attacks over the course of the previous two years, as effectively as interferon. It appears to act by causing immune tolerance of the lymphoctes with respect to myelin constituents.

Natalizumab (Tysabri) is a monoclonal antibody directed against the leukocytes integrin alpha-chain. It can be proposed in remitting MS, either as frontline treatment in severe cases (two attacks in one year with sequelae) or after failure of interferons (one attack in one year despite the treatment).

Gilenya (fingolimod) belongs to the sphingosine-1-phosphate (S1P) receptor modulator class. The indications are the same as those of natalizumab, namely the remitting forms with attacks after failure of interferons. An international trial is currently ongoing in order to evaluate the efficacy in the primary progressive forms of MS (results not available).

Fampyra is a preparation of fampridine (4-aminopyridine, 4-AP or dalfampridine) in the form of a sustained-released tablet. This medicament is indicated for the treatment of the sequelae, in particular of the problems in walking which occur during the remitting forms with sequelae or the progressive forms of the disease. Studies have shown that Fampyra improves walking in a small proportion of patients.

In the severe forms, the use of immunosuppressants, among which mitoxantrone, which is more effective than corticoids, but which comprises many more side effects, can be proposed. Social and psychological care is necessary, through integration into patient groups, keeping a job and, as required, adaptation of the workstation, psychotherapy, treatment for depression or for an anxious state.

It is important to underline that, while the immunosuppressant or immunomodulatory treatments which are aimed at inhibiting the inflammatory reaction are effective, at the beginning of the disease, in decreasing the number or the duration of the active lesions, they have only very little effectiveness on the long-term handicap and have only little or no effectiveness in the progressive (primary or secondary) forms of the disease. As regards the sequelae, only Fampyra looks to be a medicament capable of improving walking in certain patients.

Biotin (or vitamin H) is a ubiquitous water-soluble vitamin which is naturally found in many foods, such as offal, eggs and certain vegetables. In mammals, biotin acts as a cofactor for four metabolism carboxylases involved in several key steps of energy metabolism, including pyruvate carboxylase (neoglucogenesis), 3-methylcrotonyl CoA and propionyl CoA carboxylases (catabolism of certain amino acids which supply the Krebs cycle with intermediate metabolites), and acetyl CoA carboxylase (fatty acid synthesis).

Over the past few years, it has also been shown that biotin can regulate the expression of numerous genes via a mechanism of biotinylation/debiotinylation of histones, which are protein structures that regulate DNA conformation and, in so doing, the access of certain regions of the genome to transcription factors. It appears that a large number of genes of which the expression is regulated by biotin encode proteins involved in energy metabolism (Zempleni et al. 2009).

Patent application WO 2011124571 describes the use of biotin at a high dose (of the order of 100 to 600 mg/day) for the treatment of visual impairments, in particular related to optic atrophy. It should be noted that the visual impairments actually described in this application are symptoms related to a particular leukoencephalopathy, i.e. an involvement of the white matter of the brain. This document neither describes nor suggests that biotin could be used for the treatment of multiple sclerosis. Indeed, even though certain symptoms may be similar (visual problems), the etiology is quite different.

Although biotin is indicated in children with a deficiency in biotinidase or in holocarboxylase synthase, pathology conditions which are sometimes associated with leukoencephalopathy or with optic neuropathy, the doses necessary are of the order of 10 mg/day during these diseases (review in Wolf, 2010).

In the context of the present invention, it has been shown that biotin, in particular at a nigh dose, can make it possible to improve the condition of patients suffering from multiple sclerosis.

As it will be seen in the examples, although this improvement has been observed, in two patients with progressive retrobulbar optic neuritis, biotin can be used in patients exhibiting other syndromes, the etiology of the disease remaining the same (demyelinization). This is confirmed by the results obtained in a patient with homonymous lateral hemianopsia caused by damage to the cerebral optic radiations.

The invention thus relates to biotin for use thereof in the treatment of multiple sclerosis.

Also subjects of the invention are compositions containing biotin for the use thereof in the treatment of multiple sclerosis, and also the use of biotin for the production of a medicament intended for the treatment of multiple sclerosis. The teachings of the invention thus make it possible to implement treatment methods comprising the administration of biotin to patients suffering from multiple sclerosis.

In particular, the biotin can be used for the treatment of the progressive forms of multiple sclerosis (primary or secondary progressive forms).

Likewise, the biotin is used, in the treatment of multiple sclerosis, in order to allow treatment of the sequeiae observed in the relaxing/remitting form, after the attacks.

It can be used alone or in combination with another compound used for treating multiple sclerosis, in particular a compound as described above. The invention therefore covers a composition containing biotin and also another medicament against multiple sclerosis, for simultaneous, separate or sequential (spread out over time) use in the treatment of multiple sclerosis.

The biotin is preferentially administered at a high dose, i.e. at a dose greater than 50 mg per day. Even if a maximum dose is not really envisaged, the latter should not generally exceed 500 mg or 700 mg per day. In that way, a dose at least equal to 1 mg/kg/day, preferably 3 mg/kg/day, preferably 5 mg/kg/day, or at least equal to 7.5 mg/kg/day, or even. around 10 mg/kg/day, is administered to the patient. Between 50 and 700 mg of biotin per day are thus administered to the patients, generally between 50 and 500 mg per day, more preferably between 100 and 300 mg per day, generally around 300 mg per day.

In one particular embodiment which is preferred (in particular for problems of ease of use by the patient), the biotin is in a form suitable for oral administration. This therefore involves a composition for oral administration, which will contain at least 20 mg, preferably at least 40 mg of biotin, or even 50 mg, 75 mg, 100 mg, 150 mg or 250 mg of biotin. This composition is preferentially for pharmaceutical use, and is therefore a medicament. It is understood that each unit dose of this composition contains at least 20 mg, preferably at least 40 mg, or even 50 mg, 100 mg, 150 mg or 250 mg of biotin, as active ingredient.

In one particular embodiment, this composition for oral administration contains biotin as sole active ingredient, and also excipients, without any other active ingredient.

An excipient should be understood to mean any compound forming part of the formulation which is intended to act as a simple support, i.e. which is not intended to have a biological activity.

This composition can be in any form known in the art. In particular, it is in the form of gel capsules, tablets (optionally film-coated), pills or lozenges. In another embodiment, it is in the form of a syrup. Said syrup contains an amount such that it contains at least 20 mg, preferably at least 40 mg, or even. 50 mg, 75 mg or 100 mg of biotin per unit dose. The concentration of biotin in this syrup depends on the unit dose that it is desired to give to the patient.

Excipients which can be used by those skilled in the art are well known in the art. Talc (E553b), microcrystalline cellulose, lactose, starch (in particular corn starch), magnesium stearate (E572) and stearic acid (E570) can thus be chosen. This list is not exhaustive.

When this composition is prepared in the form of 25 gel capsules, a preferred excipient is microcrystalline cellulose.

When the composition is in the form of a film-coated tablet, said film-coating may be formed from any substance known in the art, such as hypromellose (E464), ethylcellulose, macrogol, talc (E553b) titanium dioxide (E171) or iron oxide (E172).

The active ingredient may also be coloured (by any acceptable colouring, such as cochineal), thereby making it possible to verify that the biotin is well dispersed in the excipient.

In another aspect, the biotin may be in the form which allows administration by injection: this then involves an injectable composition containing at least 20 mg, preferably at least 40 mg, or even 50 mg, 75 mg, 100 mg, 150 mg or 250 mg of biotin per unit dose.

This injectable composition may be in the form of a vial containing the biotin, and also acceptable excipients. The concentration of biotin is adjusted according to the envisaged volume of the vial. Certain excipients which improve biotin solubility can be used.

The excipients that can be used for the production of injectable compositions are well known in the art. Mention may in particular be made of sodium dihydrogen phosphate, sodium bicarbonate (E550i), methyl para-hydroxybenzoate (E218) and propyl para-hydroxybenzoate (E216), which can be used together in proportions that those skilled in the art are capable of determining. The water used is water for injection. The injection is preferably carried out intramuscularly. It can also be carried out intravenously.

DESCRIPTION OF THE FIGURES

FIGS. 1A-1H: Change in the visual fields (automated. campimetry) of patient 3 before and after treatment with biotin (100 mg/day) begun on Apr. 12, 2012. FIGS. 1A to 1D: right eye; FIGS. 1E to 1H: left eye. FIGS. 1A, 1E: November 2010; FIGS. 1B, 1F: December 2010; FIGS. 1C, 1G: January 2012; FIGS. 1D, 1H: 30 Jun. 2012. The absence of spontaneous modification of the visual field between November 2010 and January 2012 on three successive examinations should be noted (FIGS. 1A-1C and FIGS. 1E-1G). The improvement in the visual field in the upper left quadrant in June 2012, two months after introduction of the biotin treatment, should be noted (FIGS. 1D and 1H). The improvement is marked. by lightening of the computer plot (arrows).

EXAMPLES

Three patients with a progressive form of multiple sclerosis received biotin.
Description of Clinical Cases
Patient 1

This 72-year-old patient had progressive multiple sclerosis with optic involvement: right predominant rapid. visual acuity decrease approximately three years before the treatment.

Three months after the beginning of these problems, the patient received 3 infusions of corticoids which led to a significant but transient improvement in her visual acuity. Two further series of infusions were carried out 5 and 7 months after the beginning of the sight problems, without any notable effect.

Nine months after the beginning of the problems, the visual acuity continued to decrease, going to 1/10 on the right and 5/10 on the left. Eleven months after the beginning of the problems, she could. only count fingers on the right and the visual acuity went to 2/10 on the left.

The patient also had paroxysmal problems with walking, described as balance problems associated with lower limb weakness which each time lasted less than 24 hours.

Two years after the beginning of the problems, treatment with biotin was begun at the dose of 100 mg three times a day.

Three months later, the patient noted an improvement in her visual acuity: she could read telephone numbers, she could make out faces and could read newspaper headlines. The visual acuity was noted at 2/10 on the left and 5/10 on the right. Balance was more assured, in particular when turning round. She could cook alone, which was not the case previously. The MRI was unchanged, as was the brain MRI spectro. On the other hand, the visual evoked potentials showed the reappearance of a P100 wave on the left (no response was noted on the right) of prolonged latency (126.5 ms).

The treatment was continued at the same dose. After six months of treatment, the evoked potentials showed the beginnings of a P100 wave on the right and also an improvement in the latency of the left P100 wave (which went from 126.5 to 111.8 ms,). The brain MRI spectro showed a clear decrease in the choline peak and in the choline/creatine ratio. The treatment with biotin was increased to 600 mg/day. After nine months of treatment, a bilateral P100 wave was noted.

The treatment was then continued at the dose of 300 mg/day for 15 months, then 100 mg/day for 9 months.

Between the beginning of the treatment and the dose of the last visit, the visual acuity remained stable (2/10 on the left and 5/10 on the right) without any further episode of optic neuropathy. The balance also remained stable.
Patient 2

A man born in 1987, without any particular personal history. His family history showed that his mother had multiple sclerosis. The patient had a first neurological episode in May 2006, characterized by nystagmus, limb pain and a problem with balance, having regressed in 8 days. A second episode occurred in February 2008, characterized by fatigue, an episodic sensation of double vision and problems with balance, related to a static cerebellar syndrome. The search for an autoimmune disease was negative. The medullary MRI showed an area of hypersignal at the cervical level. The brain MRI showed numerous areas of hypersignals in the periventricular white matter, without taking contrast, the appearance of which is compatible with the diagnosis of multiple sclerosis. Treatment with interferon Ib (betaferon) began in February 2008. The patient experienced a further diplopia-type attack in July 2008 which was regressive after Solumedrol infusions.

Between 2009 and 2012, without the patient having a further attack of his disease, he indicated a very insidious and progressive decrease in his visual acuity. Although the visual acuity was considered to be normal in 2008, in July 2010 the visual acuity of the right eye was noted at 2/10 and that of the left eye at 6/10. The evoked potentials (July 2010) show a bilateral slowing of the P100 waves to 140 milliseconds, attesting to bilateral involvement or the optic. nerves. Three Solumedrol infusions were carried out in September 2010 and then 4 infusions between 8 and 11 August 2011, without any effect. The visual acuity in December 2011 went to 1/10 on the right and 3/10 on the left. The papillae are bilaterally pale. OCT (Optical Coherence Tomography) shows a considerable fall in the thickness of the peripapillary nerve fibres to 65 microns on the right and 61 microns on the left, confirming the bilateral involvement of the optic nerves. The Goldmann visual field shows two central and cecocentral scotomas and also an enlargement of the blind spot on the right side with a slight degradation compared with the previous visual field. On the left side, the existence of a central scotoma, which is also slightly enlarged compared with the previous visual field, is noted.

The successive MRIs between 2008 and 2011 do not show any increase in the damage load, indicating that the patient has a progressive form of multiple sclerosis characterized by involvement of the optic nerves.

Treatment with biotin was then introduced on 6 Mar. 2012 at the dose of 100 mg/day until 30 March and then 200 mg/day from June 4 to Jun. 5, 2012 then 300 mg/day from Jun. 5, 2012 to Jul. 6, 2012. Two complete ophthalmological examinations were carried. out during this period of time: a first on 30 Mar. 2012, which. showed no improvement in the visual acuity compared with the examination on 6 March (before treatment), and a second on Jul. 6, 2012 (after 3 months of treatment), which showed a very significant improvement in the visual acuity of the left eye, which went from 3/10 to 7.5/10.

Patent No. 3

A 29-year-old woman with no personal or family history. In mid-October 2004, she presented a left homonymous lateral hemianposia in relation to an inflammatory lesion of the white matter located on the path of the right optic radiations. The examinations had then revealed intrathecal synthesis of immunoglobulins in the CSF and the evolvement had initially been favourable after 3 infusions of Solumedrol. The symptomology subsequently reappeared. After 3 infusions of Solumedrol and orthoptic therapy, the evolvement was marked by a functional improvement. In February 2005, the appearance of further visual problems and of a further right parieto-occipital lesion taking contrast was noted. The evolvement was gradually favourable. However, a left inferior quadrantanopia persisted. The visual acuity was at $6/10^{th}$ on the right, and $7/10^{th}$ on the left. Between 2005 and the end of 2011, fluctuations in the visual acuity were noted, with regressive periods, of worsening on corticoids in November 2005, March 2006 and October 2006, with persistence of a left homonymous lateral heminanopsia between attacks. From the end of 2008, the visual acuity has been stable at 6/10 bilaterally. This stability of the homonymous lateral hemianopsia is demonstrated by several examinations of she visual field carried out between the end of 2010 and the beginning of 2012. In the face of the lack of recovery of the visual acuity, it was decided to begin a treatment with biotin at the dose of 100 mg/day. The visual evoked potentials carried out at this time were normal, demonstrating that the visual impairment is not related to an involvement of the optic nerves themselves, but indeed to a homonymous lateral hemianopsia in relation to the lesions of the white matter of the brain affecting the optic radiations. The treatment with biotin was begun on 12 Apr. 2012 at the dose of 100 mg/day. The new examination of the visual field on 30 Jun. 2012 (after 1 and a half months of treatment) shows a clear improvement in the homonymous lateral hemianopsia (FIG. 1).

Discussion

It was therefore observed that the clinical condition of patient 1 with a secondary progressive form of multiple sclerosis improved and stabilized under treatment with biotin.

This observation was confirmed in two other patients suffering from multiple sclerosis with progressive optic neuropathy (patient No. 2) or with sequelae consisting of involvement of the optic radiations in the white matter of the brain (patient No 3).

To date, these three treated patients have shown an improvement authenticated on several parameters: magnetic resonance spectroscopy, visual evoked potentials and visual acuity for the first patient, visual acuity and visual field for the second patient, visual field (campimetry) for the third.

In the three cases, the improvement occurred within three months following introduction of the treatment, while the analysis of the retrospective data showed stability and/or progressive worsening of the visual impairment during the 2 years preceding the introduction of the treatment. In addition to the improvement, stabilization of the symptoms for the eyes for which there was less improvement was also observed.

Moreover, the motor problems of patient 1 were also corrected and were stabilized.

This represents an important advance since no treatment is currently recognized in the progressive (primary or secondary) forms of multiple sclerosis and also on the symptoms related to sequelae of the disease.

REFERENCES

Anagnostouli M, Livaniou E, Nyalala J O, Evangelatos G, Zournas C, Ithakissios D S, Papageorgiou C. Cerebrospinal fluid levels of biotin in various neurological disorders. Acta Neural Scand, 1999 June; 99(6): 387-92.

Chaudhuri A, Behan P O. Multiple sclerosis is not an autoimmune disease. Arch Neurol. 2004 Oct; 61 (10) 1610-2.

Dabbaqh O, Brismar J, Gascon G G, Ozand P T. The clinical spectrum of biotin-treatable encephalopathies in Saudi Arabia. Brain Dev. 1994; 16 Suppl:72-80.

Debs R, Depienne C, Rastetter A, Bellanger A, Degos B, Galanaud D, Keren B, Lyon-Caen O, Brice A, Sedel F. Biotin-Responsive Basal Ganglia Disease (BBGD) in Europeans with novel SLCI9A3 mutations. Arch Neural. 2010 Jan; 67(1): 126-30.

Noseworthy J H, Ducchinetti C, Rodriguez M, Weinshenker B G. Multiple sclerosis. N Engl J Med. 2000 Sep 28; 343(13): 938-52.

Ozand P T, Gascon G G, Al Essa H, Joshi S, Al Jishi E, Bakheet S, Al Watban J, Al-Kawi H Z, Dabbagh O. Biotin-responsive basal ganglia disease: a. novel entity. Brain. 1998 Jul; 121 (Pt7) : 1267-79.

Polman C H, Relngold S C, Eden G, Filippi M, Hartung H P, Kappos L, et al. Diagnostic criteria for multiple sclerosis: 2005 revisions to the "McDonald Criteria". Ann Neural, 2005 Dec; 58(6): 840-6.

Ramaekers V T, Brab M, Rau G, Heimann G. (1993) Recovery from neurological deficits following biotin treatment in a biotinidase Km variant. Neuropediatrics 24: 98-102.

Sotgiu S, Pugliatti H, Fois M L, Arru G, Sanna A, Sotgiu M A, Rosati G. Genes, environment, and susceptibility to multiple sclerosis. Neurobiol Dis, 2004 Nov; 17(2):131-43

Subramanian V S, Marchant J S, Said H M. Biotin-responsive basal ganglia disease-linked mutations inhibit thiamine transport via hTHTR2: biotin is not a substrate for hTHTP2. Am J Physiol. 2006; 291(5): 851-859

Vlasova T I, Stratton S L, Wells A M, Mock N I, Mock D M. Biotin deficiency reduces expression of SLC193, a potential biotin transporter, in leukocytes from human blood. UT Nutr. 2005; 135(1): 42-47.

Weiner H L. Multiple sclerosis is an inflammatory T-cell-mediated autoimmune disease. Arch. Neural. 2004 Oct; 61(10): 1613-5.

Wolf B. Clinical issues and frequent questions about blotinidase deficiency. Mol Genet Metab. 2010 May; 100(1): 6-13

Zempleni J, Wijeratne S S, Hassan Y I. Biotin. Biofactors 2009; 35(1): 36-46.

Zeng W Q, Al-Yamani E, Acierno J S Jr et al. Biotin-responsive basal ganglia disease maps to 2q36.3 and is due to mutations in SCL19A3. Am J Hum Genet. 2005; 77(1): 16-26.

The invention claimed is:

1. A method of treating a patient suffering from multiple sclerosis, comprising administering biotin to a patient in need thereof,
wherein said multiple sclerosis is a progressive form of multiple sclerosis,
wherein treatment with biotin has a duration of at least 3 months, and to said patient at a dose of at least 1 mg/kg/day.

2. The method of claim 1, wherein said biotin is in a form suitable for oral administration.

3. The method of claim 1, wherein said biotin is in the form of a composition containing biotin and excipients, without any other active ingredient.

4. The method of claim 1, wherein said biotin is in the form of an injectable composition.

5. A method of treating sequelae attributable to multiple sclerosis attacks in a patient, comprising administering biotin to a patient in need thereof, wherein treatment with biotin has a duration of at least 3 months, and to said patient at a dose of at least 1 mg/kg/day.

6. The method of claim 5, wherein said biotin is in a form suitable for oral administration.

7. The method of claim 5, wherein said biotin is in the form of a composition containing biotin and excipients, without any other active ingredient.

8. The method of claim 5, wherein said biotin is in the form of an injectable composition.

9. The method of claim 1, wherein the biotin is administered with one or more of interferon beta, glatiramer acetate, natalizumab, fingolimod, fampridine and mitoxantrone.

10. The method of claim 5, wherein the biotin is administered with one or more of interferon beta, glatiramer acetate, natalizumab, fingolimod, fampridine and mitoxantrone.

11. The method of claim 1, wherein the biotin is administered in combination with fampridine.

12. The method of claim 1, wherein the biotin administered is between 100 and 500 mg/day.

13. The method of claim 1, wherein the biotin administered is at least 300 mg/day.

14. The method of claim 5, wherein the biotin is administered in combination with fampridine.

15. The method of claim 5, wherein the biotin administered is between 100 and 500 mg/day.

16. The method of claim 5, wherein the biotin administered is at least 300 mg/day.

17. The method of claim 1, wherein the biotin administered is at least 100 mg/day.

18. The method of claim 5, wherein the biotin administered is at least 100 mg/day.

* * * * *